United States Patent [19]
Wallace et al.

[11] Patent Number: 5,951,497
[45] Date of Patent: Sep. 14, 1999

[54] PRESSURE CATHETER DEVICE WITH ENHANCED POSITIONING FEATURES

[75] Inventors: Wm. Dean Wallace, Salt Lake City; Christopher A. Cutler, Centerville; Steven R. Smith, Draper, all of Utah

[73] Assignee: Clinical Innovation Associates, Inc., Murray, Utah

[21] Appl. No.: 08/878,054

[22] Filed: Jun. 18, 1997

Related U.S. Application Data

[63] Continuation-in-part of application No. 08/706,837, Sep. 3, 1996.

[51] Int. Cl.$^6$ .............................. A61B 5/103; A61B 5/117
[52] U.S. Cl. ........................ 600/587; 600/591; 600/176; 600/561
[58] Field of Search .................................. 600/587, 588, 600/561, 591, 593, 576, 585, 159, 190, 170, 176; 604/280, 905

[56] References Cited

U.S. PATENT DOCUMENTS

| | | | |
|---|---|---|---|
| 4,407,273 | 10/1983 | Ouchi | 600/107 |
| 4,661,110 | 4/1987 | Fortier et al. | 604/256 |
| 4,785,822 | 11/1988 | Wallace . | |
| 4,963,132 | 10/1990 | Gibson | 604/256 |
| 4,966,161 | 10/1990 | Wallace et al. . | |
| 4,967,743 | 11/1990 | Lambert | 128/202.16 |
| 5,201,723 | 4/1993 | Quinn | 604/264 |
| 5,234,417 | 8/1993 | Parks et al. | 604/283 |
| 5,279,308 | 1/1994 | DiSabito et al. . | |
| 5,364,344 | 11/1994 | Beattie et al. | 604/43 |
| 5,370,640 | 12/1994 | Kolff | 604/164 |
| 5,421,323 | 6/1995 | Herrmann et al. | 600/108 |
| 5,425,362 | 6/1995 | Siker et al. | 600/587 |
| 5,427,114 | 6/1995 | Colliver et al. | 600/587 |
| 5,520,641 | 5/1996 | Behnke et al. | 604/86 |
| 5,573,007 | 11/1996 | Bobo, Sr. . | |

OTHER PUBLICATIONS

LIFE TRACE™ brochure regarding Intrauterine Pressure Catheters, 1995.
Corometrics Medical Systems, Inc. brochure regarding Intrauterine Catheter Tip Transducer, undated.
Utah Medical Products, Inc. brochure regarding Intrauterine Pressure Catheter System——Intran Plus™ IUP–400, 1990.
Utah Medical Products, Inc. brochure regarding IUP catheters, 1992.
Brochure regarding Transducer–tipped IUP catheters, undated.

*Primary Examiner*—Richard J. Apley
*Assistant Examiner*—Justine R. Yu
*Attorney, Agent, or Firm*—Trask, Britt & Rossa

[57] ABSTRACT

A pressure catheter for monitoring changes in pressure within the body is comprised of an outer tube containing a fluid channel and a closed air column having a pressure-compliant member which is deformable upon an increase in pressure. A change in pressure deforms the pressure-compliant member, which modifies the pressure in the air column, and is translated to a pressure sensor, which converts the pressure change data to an electrical signal recognizable by a fetal monitor. The outer tube employs a window extending along at least a portion of the side thereof for viewing of bodily fluids moving through the fluid channel from the body in which the catheter is inserted toward the proximal catheter end. The pressure catheter of the present invention is particularly suitable for intrauterine pressure monitoring during labor. Viewing of amniotic fluid through the window facilitates verification of proper catheter tip placement within the amniotic fluid space. Venting closures for facilitating venting of fluid through the channel are also disclosed.

61 Claims, 8 Drawing Sheets

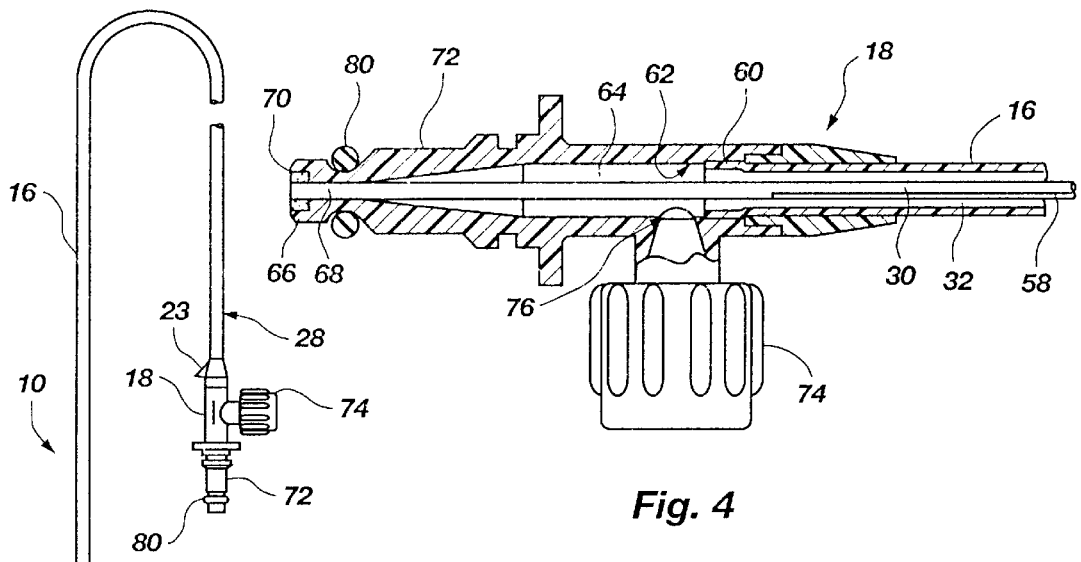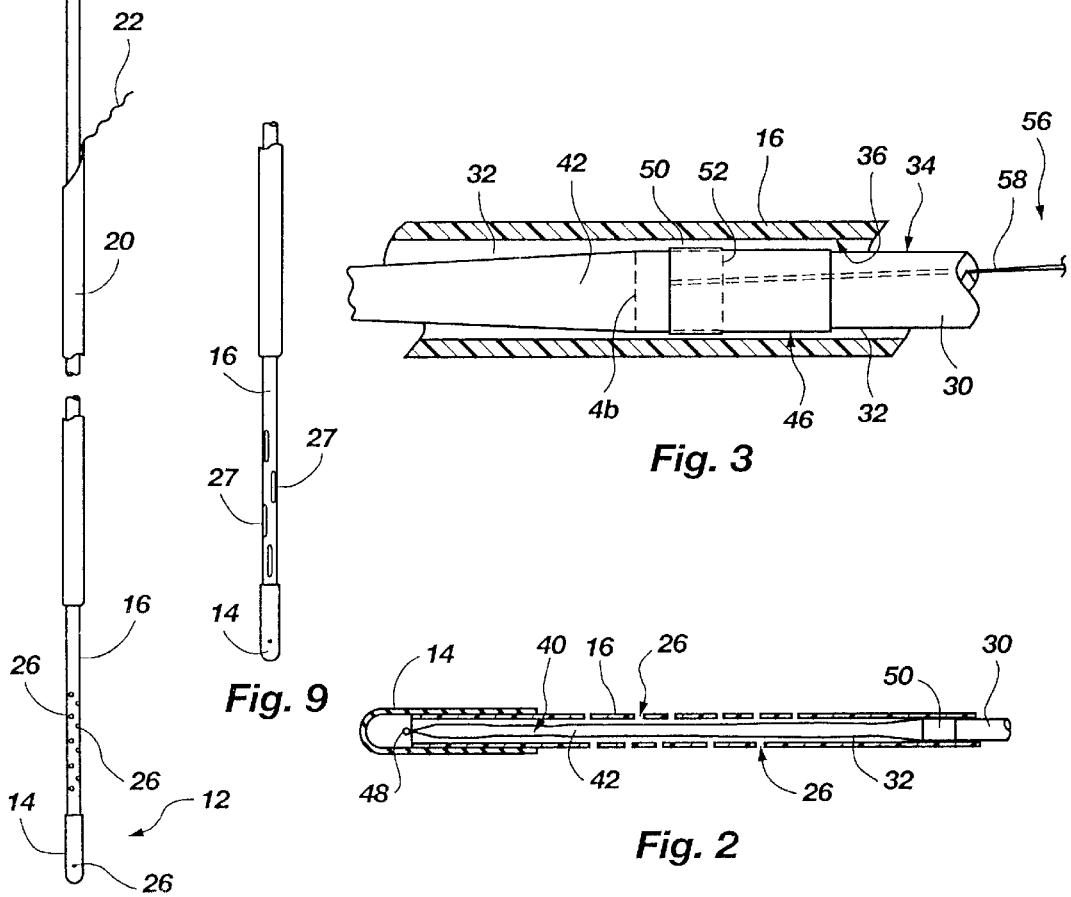

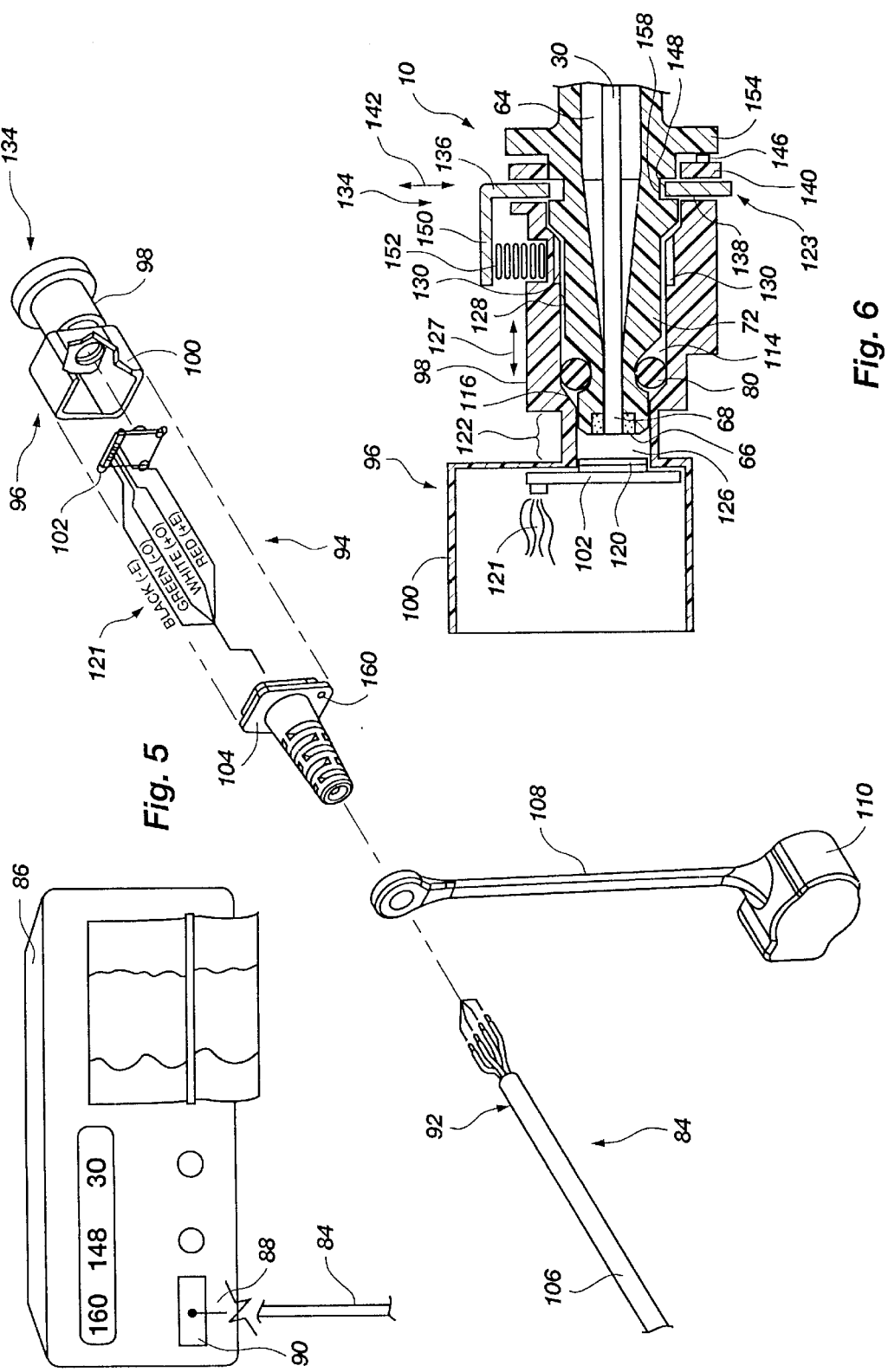

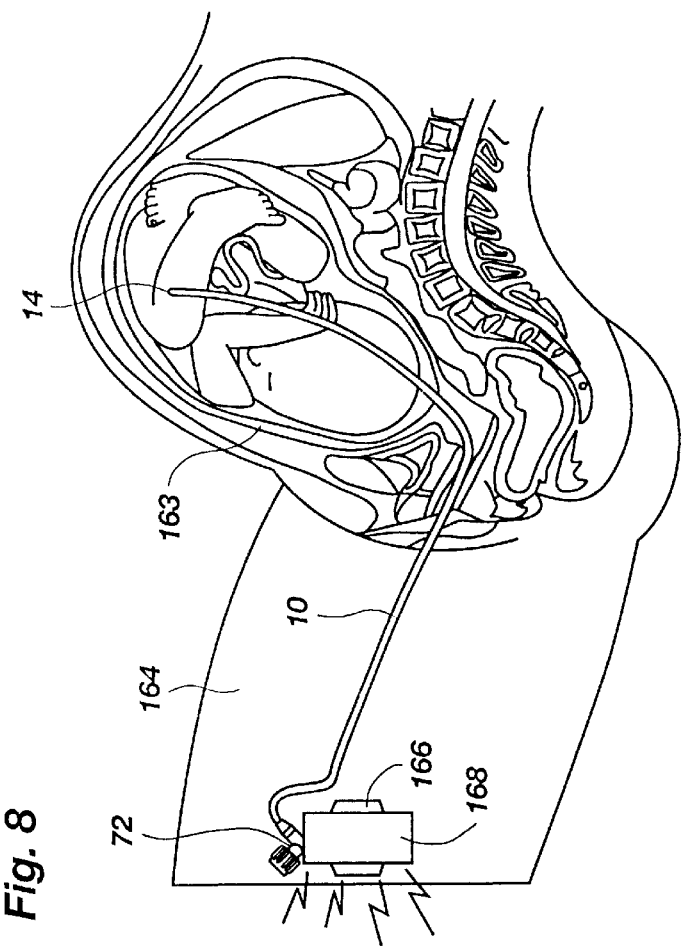
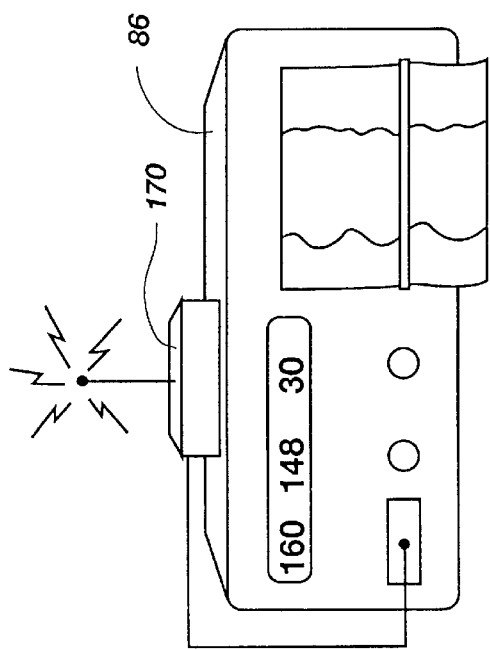
Fig. 8

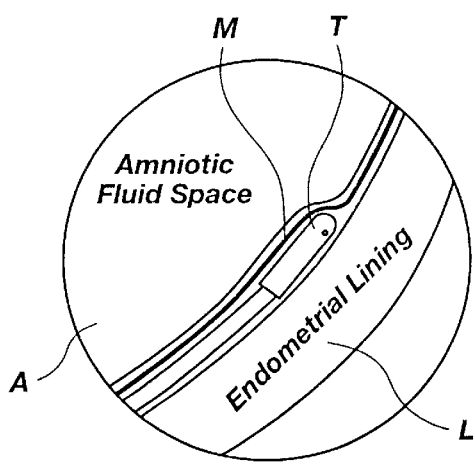
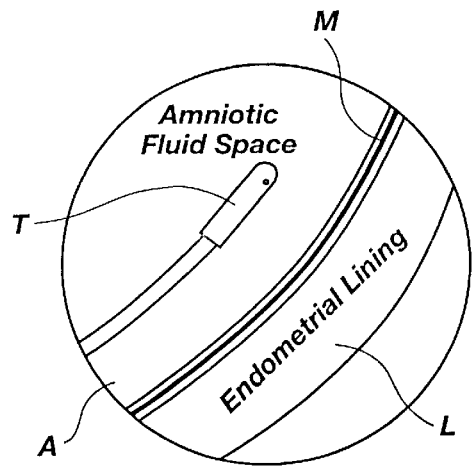
Fig. 11         Fig. 12
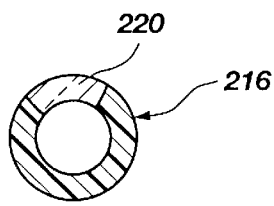
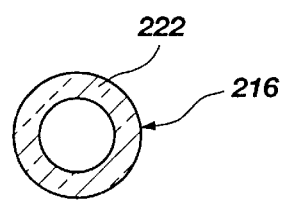
Fig. 13         Fig. 13A
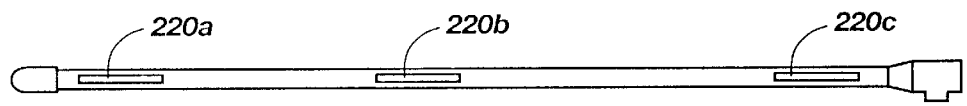
Fig. 13B

PRESSURE CATHETER DEVICE WITH ENHANCED POSITIONING FEATURES

This application is a continuation-in-part of U.S. patent application Ser. No. 08/706,837, filed Sep. 3, 1996, pending.

BACKGROUND OF THE INVENTION

1. Field of the Invention

This invention relates to devices for detecting changes in intrauterine pressure during labor. More specifically, the invention relates to catheter devices for determining pressure changes in the uterus through transference of uterine pressure to a gas-containing compliant chamber associated with a closed air column, such catheter devices including features to facilitate appropriate positioning within the uterus of a patient. Other intracorporeal applications for the catheter of the invention are also contemplated.

2. Statement of the Art

It has become common practice in the delivery and birth of a baby to monitor intrauterine conditions throughout the period of labor. Monitoring the intrauterine environment, including fetal heart rate and uterine contractions, enables the attending medical personnel to evaluate the progress of the delivery and to diagnose the existence of, or potential for, emergency situations which require immediate attention or action. Where intrauterine monitoring was once of singular importance in high risk and difficult deliveries, it has now become a routine part of the delivery procedure in many births. While only ten percent of all births are considered to be high-risk, warranting the use of intrauterine monitoring, intrauterine monitoring is used in sixty to seventy percent of all births regardless of the level of risk attributed to the birth. In actuality, about twenty percent of births experience complications.

It has long been recognized that an important relationship exists between fetal heart rate (FHR) and intrauterine pressure (IUP) and that such data relates to the well-being of the fetus during labor and delivery. Historically, two types of uterine monitoring have been practiced—external and internal. External uterine monitoring essentially comprises the attachment of a monitoring device to the mother's abdomen. The external uterine monitoring device generally detects fetal heart rate, and may have some capability for detecting intrauterine pressure or other indicia of the labor process. However, external monitoring is limited in its effectiveness because of the inaccuracy of readings obtained from the device. As uterine contractions increase, more "noise" is detected in such systems and data output becomes difficult to interpret. In addition, externally attached uterine monitoring devices move when the patient moves and, therefore, require frequent repositioning.

Known internal uterine monitoring systems, or "intrauterine" devices, include fetal scalp electrodes and pressure sensors positioned within the uterus. Internal monitoring systems are more accurate than external monitoring devices because they detect intrauterine conditions directly and thereby avoid the inaccuracy introduced by noise and other detection artifacts experienced with external uterine monitoring devices.

A number of intrauterine monitoring devices have been disclosed in the patent literature, including U.S. Pat. No. 4,785,822 to Wallace; U.S. Pat. No. 4,966,161 to Wallace, et al.; and U.S. Pat. No. 5,279,308 to DiSabito, et al. Those and other intrauterine pressure monitors employ one of two basic types of pressure detection. One type of pressure detection employs a fluid-filled tube which translates a mechanical change in fluid level within the tube to an electrical signal. A second type of pressure detection employs an electronic sensor positioned near the distal end of the device inserted in the uterus. Both types of intrauterine pressure detection devices detect timing and magnitude of changes in pressure within the uterus. Such changes within the uterus are indicative of phases of uterine contraction and relate to the well-being and status of the fetus during labor and delivery.

While intrauterine monitoring devices are more preferred than external uterine monitoring devices for the reasons given above, the performance of fluid-filled IUP devices can be problematic because the tubing of such devices can become clogged with particulate matter from the uterus or amniotic fluid. As a result, flushing and recalibration of fluid-filled IUP devices are frequently necessary. While flushing and recalibration are not difficult in such devices, the sterility of the device may be severely compromised and interruption of the monitoring procedure is inconvenient. In addition, fluid-filled IUP devices require refilling and recalibration if the patient is ambulatory. Therefore, use of such fluid-filled IUP devices may limit the ability of the patient to move or walk around during long periods of labor.

Recognizing the drawbacks and inherent problems associated with fluid-filled IUP devices, others have developed gas column pressure catheters for use in monitoring pressures in vessels and cavities of the human body. A catheter of such type is disclosed in U.S. Pat. No. 5,573,007 to Bobo. Gas column devices of the type disclosed in the Bobo patent are suitable for use in vessels or cavities where little or no impact may be encountered by the gas-filled chamber of the device. However, in applications where the gas-filled chamber is likely to encounter movement (e.g., the movement of a fetus in utero) or be crushed by other means such as bending of an artery or vein as the patient moves, the gas-filled chamber is crushed or deflated and proper pressure monitoring cannot be conducted. That problem has been addressed in some disclosed Bobo designs by providing dual gas-filled chambers for pressure monitoring so that if one is crushed or otherwise rendered inoperable because of surrounding conditions, presumably the other gas-filled chamber will operate.

Sensor-tipped IUP devices are the more recently developed of the IUP devices and have gained great popularity over fluid-filled devices because of the relative convenience in use. Minimal setup procedures are required with the sensor-tipped devices other than "zeroing" the device. Zeroing the device involves setting the base pressure to match that of the atmosphere while no pressure is being applied to the catheter. Once inserted, the catheter is connected to a fetal monitor using a reusable interface cable in the same way that the remote sensor of a fluid-filled catheter is connected to a fetal monitor.

Despite the advantages that sensor-tipped IUP devices present over fluid-filled IUP devices, known sensor-tipped devices still have certain disadvantages in use. For example, known sensor-tipped IUP devices have an enlarged tip to accommodate the sensor located in the tip, and the enlarged tip often causes discomfort during insertion. Discomfort is also caused by the hardness of the material used to manufacture the tip. The major disadvantage of inserting sensor-tipped IUP devices, as well as fluid-filled IUP devices, is the possibility of perforating the placenta or uterus as a result of the higher insertion force required to insert a larger tip. More incidences of perforation are experienced with sensor-tipped IUP devices, and deaths have been reported of both fetuses and mothers from damage caused by insertion of sensor-tipped devices. A sensation of tingling at the site of the sensor has also been reported by some patients due to the electrical current which runs through the IUP device to the sensor in the tip.

Further, correct placement of any intrauterine pressure catheter device within the amniotic fluid space of the uterus is important to ensure an accurate, absolute intra-amniotic pressure reading. To elaborate, when the distal end of a pressure catheter is inserted into the uterus, the clinician intends to insert it through the amniotic membranes, the amnion and chorion, and into the amniotic fluid surrounding the fetus. However, the catheter is frequently (25–50% of insertions) placed in a so-called "extraovular" position outside the amniotic membranes and between the chorion and decidua-endometrial lining. Such a placement will provide a reading, but not the reading of absolute intra-amniotic pressure. Rather, the reading provided by the extraovular placement of the distal catheter tip is comparable to external tocotonometer monitoring, which provides a relative value. Such extraovular readings exhibit high baseline pressure values and damped waveforms produced by contractions. To date, the prior art has failed to provide a means for confirming proper placement of the distal tip of the catheter which is easy to employ and which also does not place the clinician at risk from pathogens present in the amniotic fluid.

Thus, it would be advantageous to the field of obstetrics to provide an intrauterine pressure monitor which is simple in construction, which is easily and quickly calibrated for accurately monitoring pressure changes, which is structured for easy and safe insertion into the uterus, which is structured to avoid damaging the uterus or endangering the fetus, which facilitates appropriate positioning within the uterus for maximum effectiveness and without risk of clinician exposure to pathogens, which minimizes discomfort to the patient and which permits the patient to move freely without compromising the calibration or operation of the device.

BRIEF SUMMARY OF THE INVENTION

In accordance with the present invention, a disposable pressure catheter device is structured with a closed air column coupled to a pressure detection device, the air column having a pressure-compliant member which is deformable upon a change in pressure experienced within a body to translate such change in pressure through the air column to the pressure detection means. The pressure catheter device of the present invention can be adapted for use in a variety of medical procedures where changes in pressure within the body are to be detected, such as arterial pressure monitoring, cardiac pressure monitoring, pulmonary artery pressure monitoring and intracranial monitoring. However, the present invention is particularly suited for use in intrauterine pressure detection during labor and will be described herein with respect to that exemplar application.

The intrauterine pressure catheter device of the present invention is generally comprised of a catheter having an elongated outer hollow tube in which is disposed a substantially co-extensive inner tube defining an internal air column. At the proximal end of the catheter is a housing to which the outer hollow tube and inner tube are attached. The housing provides a means of connecting the catheter to a reusable interface cable, or connector, which is in turn connected to a fetal monitor unit. As used herein, "proximal" refers to that end of the pressure catheter device which is positioned outside the uterus and away from the patient's body, and "distal" refers to that end of the pressure catheter device which is positioned within or toward the uterus of the patient.

The outer hollow tube of the catheter is made from a biocompatible, flexible material. A tip is formed or applied at the distal end of the outer hollow tube to facilitate insertion of the catheter device into the uterus. The tip is most suitably made of a soft, pliant material which is readily deformable when it comes into contact with a resistive surface, such as the uterine wall or the fetus. Immediately behind the tip, toward the proximal end of the catheter, a plurality of small holes is formed through the wall of the outer hollow tube. The holes may be formed about the circumference of the outer hollow tube, and may also be positioned through the tip. The holes are sized to permit the passage of fluid therethrough, but are sufficiently small to prevent the movement of large particulates from the uterus therethrough. Alternatively, long, narrow slits may be formed through the wall of the outer hollow tube extending from near the tip to a selected distance away from the tip. The outer tube is sealed at its proximal end to the housing.

The inner tube positioned within the outer hollow tube is also made of a flexible, biocompatible material. The inner tube is smaller in outer diameter than the outer hollow tube, such that a space or passage is formed between the inner wall of the outer hollow tube and the outer wall of the inner tube. The space becomes filled with fluid following insertion of the device within the uterus. The inner tube is sealed at its proximal end to the housing, to which the outer tube is also attached. Alternatively, a dual lumen tube may be employed.

Proximate the distal end of the catheter and at the distal end of the inner tube is a pressure-compliant member which is deformable upon a change in pressure within the uterus. In the most preferred embodiment at present, the pressure-compliant member is a cylindrically-shaped balloon which is formed from a thin-walled, low durometer material, such as rubber or plastic, which is easily deformed within a given range of pressure variations. The balloon is closed at the distal end thereof and is attached at its proximal end to the open, distal end of the inner tube. As such, the inner tube and balloon define an internal closed air column which, in operation, is charged with sufficient air to maintain the balloon in a somewhat expanded state which is readily deformable in response to changes in intrauterine pressure. In a preferred embodiment, the balloon is attached to the inner tube with a flexible element, such as a resilient band, which expands to permit the escape of air from within the closed air column in the event that an excess of air pressure is present therein, thereby serving as a pressure relief valve. Although certain preferred embodiments employ balloons housed within an outer tube, a balloon disposed on the exterior of the catheter may be employed.

The balloon is positioned within the outer hollow tube so that it extends from near the distal tip of the catheter to at least within several millimeters from the tip. The holes or slits formed in the outer hollow tube are distributed about the circumference of the outer hollow tube to minimize kinking of the catheter, and the pressure-complaint member, or balloon, is positioned in lateral proximity to the holes. When the pressure catheter is positioned within the uterus and is charged with sufficient air to inflate the balloon from a totally collapsed or flaccid state, fluid fills the space between the inner tube and outer hollow tube and changes in fluid pressure within the uterus are manifested through the holes and in the fluid residing in the space. A collapsing deformation of the inflated balloon occurs with an increase in pressure, in turn leading to a detectable increase in pressure in the air column. An expanding deformation of the balloon occurs with a decrease in uterine pressure following a contraction and results in a detectable decrease in pressure in the air column. It is notable that the construction of the balloon and the material of its construction is such that no effect is experienced in the air column due to, for example, changes in temperature (i.e., the effects of Charles's Law), loss of gas due to permeability of the balloon material or water vapor absorption.

The inner tube may preferably be constructed with means for ameliorating any accumulation of condensation within the inner tube which may result from humidity in the atmosphere or from placement in the moist, warm environment of the uterus. In a preferred embodiment of the invention, a line of nylon or similarly hygroscopic material is positioned along the inner wall of the inner tube and extends from the proximal end of the inner tube to the distal end of the inner tube. The nylon line attracts moisture in the inner tube and distributes the moisture along the length of the inner tube so that any accumulation of condensation does not form in one area, such as near the distal end of the inner tube. The nylon line also adds structural reinforcement to the otherwise extremely collapsible inner tube and helps prevent complete closure of the inner tube in the event of kinking of the catheter.

The outer tube and the inner tube are both sealed to a housing which is configured as a connector for interconnecting with a reusable interface cable assembly. The outer hollow tube and inner tube are connected to the housing in a manner which provides a sealed space between the outer hollow tube and the inner tube extending to the holes or slits at the distal end of the outer tube. The housing is, most suitably, structured with an amnio port which is in fluid communication with the space between the outer hollow tube and the inner tube. Thus, amniotic fluid can be withdrawn from the uterus through the holes formed in the distal end of the outer hollow tube and through the amnio port. Further, fluid can be injected through the amnio port and through the space between the outer hollow tube and the inner tube for delivery to the intrauterine environment or to dislodge matter which may have temporarily occluded some of the holes formed in the outer hollow tube.

The connector of the housing is structured to closely accommodate the proximal end of the inner tube, the open end of which is positioned at the proximal extremity of the connector. An O-ring or other annular seal may, in one embodiment, be positioned about the exterior of the connector in proximity to the proximal end of the inner tube, although the inner tube may be foreshortened and a passage in the housing might extend to the proximal end thereof, the O-ring extending about the passage. The connector of the housing is sized to interconnect with a connector formed as a mating part of a coupling positioned at the distal end of the reusable interface cable assembly. In one embodiment of the invention, the connector of the reusable interface cable assembly may be structured as a female connector having a cavity which is sized to snugly receive a male connector structured as part of the housing. The female connector is structured with a selected volume which contains enough air to charge the air column, or inner tube and balloon, upon engagement of the male and female connectors. That is, as the male connector is longitudinally inserted into the female connector cavity, a small volume of air occupying a portion of the female connector means is trapped and is automatically forced into the air column during connection to at least partially inflate the balloon. The male connector, having an external O-ring, acts as a piston or plunger along the travel of the male connector into the cavity, the O-ring establishing an air-tight seal between the male and female connector elements to trap, pressurize and maintain an appropriate amount of air in the air column. In an alternative embodiment, the housing to which the outer hollow tube and inner tube are connected may be formed as a female connector having a cavity sized to receive a male connector structured at the distal end of the reusable interface cable.

A coupling formed at the distal end of the reusable interface cable assembly may preferably house a pressure detection device, such as a pressure transducer. In the presently preferred embodiment, the coupling houses a pressure transducer having a diaphragm which is positioned in close proximity to the open proximal end of the inner tube when the male connector is fully inserted into the female connector and the air column is charged. Thus, as pressure within the uterus increases, an increase in fluid pressure brought about by an increase in fluid pressure across the holes or slits in the outer hollow tube applies sufficient pressure to the balloon to deform (i.e., partially collapse) the balloon slightly. The change in pressure exerted on the air column with deformation of the balloon is translated through the air column to the diaphragm of the pressure transducer, and the change in pressure is detected by the pressure transducer. The transducer is in electrical communication, via the reusable interface cable of the assembly, with a fetal monitor which provides a reading of the pressure change.

In operation, the intrauterine pressure catheter of the present invention is inserted through the vagina and into the uterus by known techniques of intrauterine pressure catheter placement. A removable introducer sheath may be initially positioned about the outer tube of the catheter to assist in placement of the IUP catheter. Once the IUP catheter is positioned, the introducer sheath is drawn rearwardly toward the proximal end of the outer tube. The housing of the catheter may be formed with a protrusion against which the introducer sheath may be contacted to initiate a slit in the sheath. The sheath is then removed from about the outer tube and is discarded. Upon initial insertion into the uterus, the pressure-compliant member, or balloon, is substantially empty (i.e., not filled with air). The male connector of the housing, in a first embodiment, is inserted into the female connector cavity of the coupling of the reusable interface cable assembly. With insertion of the male connector into the female connector of the reusable interface cable assembly, the air column becomes charged, or filled with air. The pressure-compliant member is, as a result, at least partially filled with air and the membrane of the pressure-compliant member is primed for pressure sensing. The electrical connector at the proximal end of the reusable interface cable assembly is then plugged into the fetal monitor and the monitor is powered on. The proximal end of the IUP catheter may conveniently be taped to the thigh of the patient to keep the catheter in place.

The IUP catheter of the present invention is configured so that the patient may move without compromising the calibration or placement of the catheter. The present invention, therefore, provides a particular advantage over known devices since the sensor device of the present invention can be reset, or "zeroed", at any time if the patient's movements should compromise the charge in the air column. The device can even be reset while positioned in the uterus, which is not typically possible with known devices. In one embodiment of the present invention, the patient may be attached to the fetal monitor by the reusable interface cable and is, therefore, restricted in mobility. In an alternative embodiment, a wireless telemetry unit may be used which includes a reusable transmitter unit having a connector and an associated pressure detection device as previously described, which is attachable to the connector of the housing and a reusable remote receiver which is attached to the fetal monitor. Intrauterine pressure changes may then be monitored on a constant basis even while the patient is ambulatory, the pressure detection data being sent to the fetal monitor through the telemetry unit.

An additional benefit is provided in one embodiment of the catheter of the invention in the form of a transparent or translucent view window extending longitudinally along at least a portion of the wall of the hollow outer tube. The view window provides a view of amniotic fluid traveling from the distal end of the catheter toward the proximal end, through the channel defined between the outer tube and the inner tube. The window may extend longitudinally along substantially the entire length of the outer tube, and circumferentially along a suitable arc, for example 75 degrees, of the outer tube wall. Alternatively, the entire outer tube may be made of an ambient light-penetrable material for easy viewing of amniotic fluid. Preferably, the windowed outer tube is employed with a closure providing a venting function, so that the channel (lumen) extending within the outer tube (between the base wall of the outer tube and the exterior of the inner tube) may be exposed to atmospheric pressure in a controlled manner, to permit amniotic fluid to vent by dripping slowly from the proximal end of the outer tube through a small aperture in the cap. The vent cap may be provided with a manual closure capability, so that it may be sealed when amniotic fluid is viewed through the window but before traveling the length of the outer tube, thus providing an additional margin of safety against pathogen exposure for the clinician. Another embodiment of a venting closure may comprise a plug or other closure including a gas-permeable, porous element. The porous element permits venting therethrough of air in the outer tube channel or lumen, but is liquid-impermeable due to the small pore size in the element, and which will also desirably block passage of bacterial or viral pathogens. With such an arrangement, the amniotic fluid may flow relatively freely to the venting closure, pushing the air in the lumen ahead of it until the liquid contacts the element, which acts as a seal or barrier. This feature also provides an automatic method for venting air out of the outer tube lumen, so that if amnio infusion is required, there will be negligible air in the lumen, obviating the potential for inadvertent air injection into the amniotic cavity during infusion. Of course, the venting closure may be removed as desired for sampling, amnio infusion, or other purposes. Thus, the invention also provides the aforementioned desirable characteristics of verification of correct catheter placement with attendant safety for the clinician.

It is contemplated that the view window and venting closure features have independent utility, although beneficial when employed together. Further, it is contemplated that the view window and venting closure features have utility in applications not limited or restricted to enclosed or internal balloons. That is, catheter structures employing balloons on their exteriors, or partially interior and partially exterior, will also benefit from the presence of view windows and venting closures.

Further, a single tube, two-lumen catheter may be fabricated with a view window extending along an exterior wall of one lumen, or the entire tube fabricated of a light-transmissive material. Alternatively, two adjacent tubes may be employed, with at least one formed of light-transmissive material or having a longitudinally-extending view window or windows.

BRIEF DESCRIPTION OF THE SEVERAL VIEWS OF THE DRAWING

In the drawings, which illustrate what is presently considered to be the best mode for carrying out the invention:

FIG. 1 is a view in elevation of the intrauterine pressure catheter of the present invention;

FIG. 2 is an enlarged view in longitudinal cross section of the tip of the intrauterine pressure catheter shown in FIG. 1;

FIG. 3 is an enlarged view in cutaway longitudinal cross section of the attachment of the pressure-compliant member of the catheter to the inner tube;

FIG. 4 is an enlarged partial longitudinal cross section of the proximal end of the intrauterine pressure catheter showing the housing illustrated in FIG. 1;

FIG. 5 is an exploded view of the end of the reusable interface cable assembly with the female connector and housing the pressure detection device, the cable of the assembly extending as shown to a monitor;

FIG. 6 is an enlarged view in longitudinal cross section illustrating the male connector of the housing inserted in the female connector of the reusable interface cable assembly;

FIG. 8 is a view in partial cutaway illustrating an alternative means of monitoring intrauterine pressure changes using the invention via wireless telemetry;

FIG. 9 is an enlarged view in elevation of the distal end of the catheter of an alternative embodiment;

FIG. 11 is a side view of extraovular placement of the distal tip of a catheter;

FIG. 12 is a side view of proper placement within the amniotic sac of the distal end of a catheter;

FIG. 13 is an enlarged cross-sectional view of a catheter structure including a view window in a portion of the side wall of the outer tube;

FIG. 13A is an enlarged cross-sectional view of a light-transmissive outer tube structure;

FIG. 13B is a side schematic view of an outer tube structure including a plurality of longitudinally-spaced view windows;

DETAILED DESCRIPTION OF THE INVENTION

Figure 7:
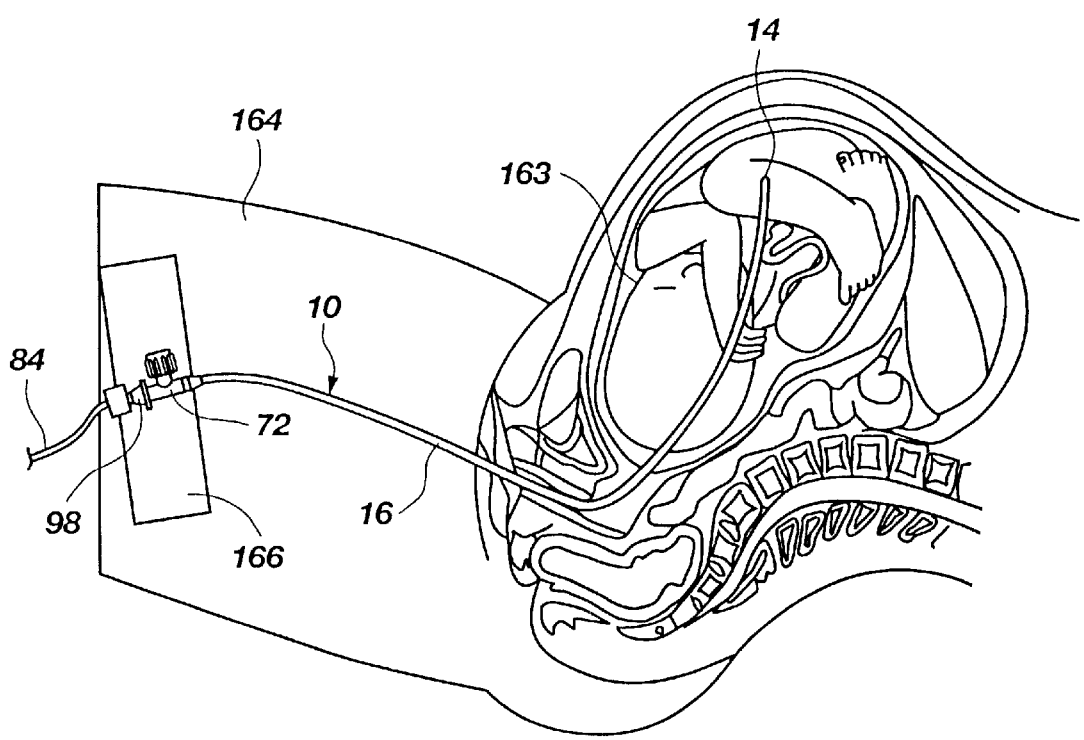
FIG. 7 is a view in partial anatomical cutaway illustrating the insertion of the intrauterine pressure catheter within the uterus of a patient and the attachment of the housing to the patient's leg.

FIG. 1 illustrates the disposable intrauterine pressure (IUP) catheter 10 of the present invention. At the distal end 12 of the catheter 10 there is formed a soft, pliant tip 14 which facilitates insertion of the IUP catheter 10 into the uterus. The soft tip 14 may preferably be formed of a material which is pliant enough to deflect or give as the tip 14 encounters a resistive force, such as the fetus, placenta or the uterine wall. A low durometer plastic or elastomer, such as polyvinyl chloride (PVC) or a polyurethane, is highly suitable. The tip 14 is attached to an elongated outer hollow tube 16 which extends from the tip 14 at its distal end to a housing 18 at its proximal end. The outer hollow tube 16 is formed of flexible, biocompatible material, such as PVC or a polyolefin, with sufficient wall thickness to resist collapse under normal conditions, and sized in length to extend from within the uterus of a patient to outside the body of the patient, as illustrated in FIG. 7. Thus, for example, the outer hollow tube 16 may range in length from 60 cm to 90 cm. A tear-away sheath 20 may be initially positioned about the outer hollow tube 16 to facilitate insertion of the IUP catheter 10 into the uterus. After insertion of the IUP catheter 10, the tear-away sheath 20 is removed, such as by pulling on thumb tab 22 and slitting against a ramp or other protrusion 23 on the proximal end of catheter 10.

A plurality of holes 26 is formed through the wall of the outer hollow tube 16 immediately behind the tip 14. The pattern of holes 26 may vary, but preferably the holes 26 are distributed about the circumference of the outer hollow tube 16 and longitudinally therealong to allow fluid to enter into the outer hollow tube 16 from any direction thereabout. A plurality of holes 26 is provided so that if any one or more holes 26 should become clogged with matter from the amniotic fluid, other holes 26 will be available for allowing passage of fluid, and transmission of fluid pressure, therethrough. The holes 26 extend for a distance beyond the tip 14 in the direction of the proximal end 28 of the outer hollow tube 16. The holes 26 may extend anywhere from one millimeter to several centimeters beyond the tip 14. One or more holes 26 may also be formed through the tip 14. In an alternative embodiment, slits 27 may be formed through the wall of the outer hollow tube 16 as shown in FIG. 9. It is preferable that the holes or slits extend distal to the most distal end of the balloon 42 disposed within tube 16 so that excessive infusion of fluid entering tube 16 will flush debris past the balloon if such had accumulated (such as vernix, meconium, etc.).

An inner tube 30 is disposed within the outer hollow tube 16, as shown more fully in FIGS. 2–4. The inner tube 30 extends from the housing 18, to which it is sealed, to near the distal end 12 of the IUP catheter 10. The inner tube 30 is hollow and is made of flexible, biocompatible material, such as polyurethane. The inner tube 30 is sized in diameter to fit within the outer hollow tube 16 and to leave a space or passage 32 between the outer wall 34 of the inner tube 30 and the inner wall 36 of the outer hollow tube 16, as best shown in FIG. 3. Inner tube 30 is preferably a "bump" tube, of increasing outer diameter (o.d.) toward the distal end thereof. The space 32 becomes filled with fluid following insertion of the IUP catheter 10 into the uterus.

A pressure-compliant member 40 is associated with the inner tube 30 and is positioned within the relatively noncompliant outer hollow tube 16 for protection against direct extreme pressure conditions exerted by surfaces (i.e., the uterine wall or fetus) or objects within the intrauterine environment. The pressure-compliant member 40, which is air-filled, as will be described below, is structured to deflect or deform upon an increase in pressure within the uterus, and to expand again upon a subsequent decrease in pressure. Therefore, a particularly suitable pressure-compliant member 40 may be a balloon 42 formed of a thin-walled, flexible, low durometer material such as C-Flex® elastomer, which is relatively easily deformed with a small increase in pressure. As shown in FIG. 2, the balloon 42 may be formed as an elongated, cylindrical body which is disposed about and attached to the open, distal end 46 (FIG. 3) of the inner tube 30 and which is heat-sealed at the distal end 48 of the balloon 42. The balloon 42 may be positioned within the outer hollow tube 16 to extend from the distal end 46 of the inner tube 30 to near the extremity of the tip 14. The balloon 42 may generally have an outer diameter (o.d.) approximately equal to the o.d. of the inner tube 30 such that a space or lumen 32 is formed between the balloon 42 and the inner wall 36 of the outer hollow tube 16.

Air occupies the interior of the inner tube 30 and is at atmospheric pressure prior to use of the IUP catheter. The inner tube 30 and the balloon 42 attached to the inner tube 30 may, therefore, form or define an air column which extends from the housing 18 to near the tip 14 of the IUP catheter 10. When the IUP catheter 10 is attached to an interface cable, as explained further below, the air column becomes filled, or "charged," with an additional quantity of air. The additional air charged into the air column fills the balloon 42, at least partially, to a selected volume. The material of the balloon 42 is very pliant due to its thin wall and the low durometer material used in its construction, and the balloon 42 deforms easily, and substantially without artifact introduced by the material of the balloon itself, with a given change in pressure external to the balloon 42. The material of the balloon may, for example, be about a 30 A Shore durometer hardness. A particularly suitable material for use in forming the inner tube 30 may be C-Flex® synthetic elastomer (Consolidated Polymer Technologies, Inc., Largo, Fla.) of 0.001–0.002 in. (1–2 mil) wall thickness, or any other similar material having similar durability and flexibility. Regardless of the material employed, less than 5 mm Hg of maximum external pressure should be required to collapse balloon 42 when its interior is vented to atmospheric pressure. The uterus typically has a 5–30 mm Hg resting tone, and therefore will ensure collapse of balloon 42 upon insertion of catheter 10 and before charging. The collapse of balloon 42, before charging the air column as subsequently described, provides an accurate pressure signal.

The balloon 42 may be attached to the distal end 46 of the inner tube 30 in any appropriate manner. However, as illustrated in FIG. 3, the balloon 42 may preferably be attached to the inner tube 30 by a resilient, elastomeric band 50 which surrounds the circumference of the proximal end 52 of the balloon 42 which is positioned over the distal end 46 of the inner tube 30. The resilient band 50 is sufficiently strong to maintain the proximal end 52 of the balloon 42 on the inner tube. 30, but is sufficiently resilient to release any excess air pressure above a predetermined threshold pressure. It should be understood that too high an internal air column pressure will reduce the sensitivity of the device for measuring pressure changes and will increase the susceptibility of the pressure monitoring to temperature-induced artifacts. Balloon 42 may burst due to its relatively fragile construction if over-pressurized.

The balloon 42 is positioned within the outer hollow tube 16 to be substantially laterally aligned with the holes 26, or slits 27, which are formed through the outer hollow tube 16. In an exemplary embodiment, the balloon is about 5 centimeters long, while the holes are placed over a 7–8 centimeter range from the tip 14, thus allowing fluid to pass by the balloon as previously mentioned. The extended hole pattern also addresses short occlusion areas due to contact by the uterus. Thus, when the IUP catheter 10 is positioned within the uterus, fluid fills the space 32 formed between the outer hollow tube 16 and the inner tube 30, thereby substantially surrounding the balloon 42 with fluid and providing a lubricating effect to alleviate sticking of the balloon 42 to the inner wall 36 of the outer hollow tube 16. Very small matter from the amniotic fluid may also enter through the holes 26 and occupy the space 32. To avoid any sticking of the inner tube 30 to inner wall 36 of the outer hollow tube 16, brought about by the existence of matter in the space 32, the exteriors of inner tube 30 and balloon 42 may be coated during manufacturing with a surfactant which, upon wetting, provides a slippery coating which prevents the inner tube 30 from sticking to the inner wall 36. One example of a suitable surfactant is sodium lauryl sulfate. The inner tube 30 and balloon 42 may also be exterior-coated with an anticoagulant to prevent clotting of blood cells in the space 32 and about the inner tube 30.

The air column formed in the inner tube 30 and balloon 42 may have an amount of condensation associated therewith as a result of ambient humidity or minute amounts of water permeating through the balloon 42 or through the inner tube 30 after the IUP catheter 10 has been positioned in the uterus (which averages a temperature of about 37° C.) for a period of time. To avoid an accumulation of condensation in the air column, therefore, the inner tube 30 may be structured with a moisture-collecting element 56 to draw or collect moisture within the tube 30. As shown in FIG. 3, the moisture-collecting element 56 may suitably be a line or strand 58 of hygroscopic material, such as nylon, which collects condensate and wicks and distributes the moisture along the length of the line 58. The absorbent line 58 may preferably extend from the distal end 46 of the inner tube 30 to near the proximal end 28 of the hollow outer tube 16. The line may be, for example, approximately 0.01 inch (10 mil) in diameter and is anchored to the interior wall of inner tube 30 by application of a drop of adhesive applied at the distal end of the tube, the line material drawing the adhesive along the line into the tube. The other end of line 58 is free, but the line is rigid enough to maintain itself in place with one anchor point. The absorbent line 58 also provides a degree of structural support against collapse to the inner tube 30, which helps prevent the otherwise flexible inner tube 30 from kinking and compromising the air column, and prevents total closure of inner tube 30 upon kinking.

As shown in FIG. 4, both the outer hollow tube 16 and the inner tube 30 are attached to the housing 18 in sealing engagement therewith. The proximal end 60 of the outer hollow tube 16 is attached to the inner surface 62 of the housing 18. The inner tube 30, which extends through the outer hollow tube 16, enters through the interior lumen 64 of the housing 18 and extends to the proximal extremity 66 of the housing 18. The proximal end 68 of the inner tube 30 is sealed to the proximal extremity 66 of the housing 18 by any suitable means, such as by a sealing gasket and/or adhesive 70. The proximal end 68 of the inner tube 30 remains open. In the embodiment of the device illustrated in FIGS. 4 and 6, the housing 18 is structured with a male connector 72 which is sized to be inserted into a female connector of a reusable interface cable assembly as described more fully hereinafter. The male connector 72 of the IUP catheter 10 includes an O-ring or other annular seal element 80 which facilitates an air-tight seal between the IUP catheter 10 and the reusable interface cable assembly (FIG. 5).

The housing 18 may also be formed with an amnio port 74 having an opening 76 which communicates with the interior lumen 64 of the housing 18. The interior lumen 64 is contiguous with the space 32 formed between the inner tube 30 and the outer hollow tube 16. Therefore, fluid entering the space 32 from the amniotic environment may be sampled or withdrawn from the amnio port 74. Alternatively, fluid may be injected into the uterine environment through the amnio port 74. In particular, a bolus of fluid can be injected into the amnio port 74 to flush the holes 26 formed near the tip 14 of the IUP catheter 10, thereby dislodging any matter which may be occluding the holes 26.

The IUP catheter 10 as thus far described is detachably attached to a reusable interface cable assembly 84 which is structured to be plugged into a fetal monitor 86, as illustrated in FIG. 5. The reusable interface cable assembly 84 has, at its proximal end 88, an electrical connector 90 which is sized and configured for attachment to a fetal monitor 86. At the distal end 92 of the reusable interface cable 84 is a pressure detection device 94 which interfaces with the air column of the IUP catheter 10 to detect changes in intrauterine pressure. The pressure detection device 94 may, as shown in FIGS. 5 and 6, comprise a coupling 96 structured with a female connector 98 sized to receive the male connector 72 of the IUP catheter 10, an enclosure for retaining a pressure sensor 102 and an end cap 104 for capping the enclosure 100 and attaching the pressure detection device 94 to a tubular cable 106 of the reusable interface cable assembly 84. A protective cover 108 may also be provided on the reusable interface cable assembly 84 and have a cap 110 sized to fit over the exposed end of the female connector 98 when the reusable interface cable assembly 84 is not connected to the IUP catheter 10.

As shown more clearly in FIG. 6, the female connector 98 is attached, or integrally formed, to the enclosure 100. The female connector 98 has an internal bore or cavity 114 which is sized in internal diameter and length to snugly receive the male connector 72 of the IUP catheter 10. Upon insertion of the male connector 72 in the bore 114 of the female connector 98, the O-ring 80 becomes seated against an inner wall 128 of the internal bore 114 to form an air-tight fit. Further, the proximal extremity 66 of the housing 18 and the open proximal end 68 of the inner tube 30 are positioned in close proximity to the pressure sensor 102 retained within the enclosure 100, minimizing dead space in the system. The pressure sensor 102 may, most suitably, be a pressure transducer, such as an NPC-109 manufactured by Lucas NovaSensors of Fremont, Calif., having a deformable diaphragm 120 which is positioned toward the female connector means 98. Wiring 121 extends from the pressure sensor 102 through the enclosure 100 and to the proximal end 88 of the cable 106 for communication to monitor 86.

The bore 114 and throat 122 lying between the mouth 123 of the female connector 98 and the enclosure 100 of the coupling 96 define an internal space 126 which contains a predetermined or selected volume of air prior to insertion of the male connector 72 into the bore 114 of female connector 98. Thus, as the male connector 72 is inserted like a piston or plunger into the bore 114 of female connector 98 in the direction of arrow 127, part of the volume of air contained within the internal space 126 of the bore 114 is displaced by male connector 72. The displaced volume of air is sufficient to "charge" or fill the balloon 42 with an appropriate amount of air to expand the balloon 42 to function with desired sensitivity responsive to a given range of pressure values, as described further below. As the male connector 72 is inserted into the female connector 98 and the O-ring 80 registers against the inner wall 128 surrounding the internal bore 114, excess air is released from the internal bore 114 through indented flutes 130 formed in the inner wall 128 so that the precharge volume of air is precisely defined. Further, the fluted bore 114 aligns the male connector 72 prior to sealing by the O-ring 80. Stated another way, the effective air volume trapped in the air column is defined by the inward stroke or travel of male connector 72 from the point at which O-ring 80 passes flutes 130 until connector 72 is fully inserted in female connector 98.

The female connector 98 of the coupling 96 may be structured with a locking device 134 for retaining the male connector 72 in exact position within the female connector 98. As shown in FIG. 6, an exemplary locking device 134 may comprise a slidable ring 136 which is positioned against, and slides within, a groove 138 formed in the outer flange 140 of the female connector 98. The slidable ring 136 moves in the direction of arrow 142. A detent 146 engages a lip 148 of the slidable ring 136 when the locking device 134 is in an unlocked position and thumb tab 150 is depressed against spring 152. As the male connector 72 is inserted into the female connector 98, an outwardly extending flange 154 of male connector 72 depresses the detent 146, thereby disengaging the slidable ring 136 from its engagement with the detent 146, and the spring 152, pushing against the thumb tab 150, moves the slidable ring 136 laterally. The lip 148 of the slidable ring 136 is urged into a groove 158 formed in the male connector 72 and locks the male connector 72 in place. The male connector 72 can only be released from the female connector 98 by depressing the thumb tab 150 and engaging the detent 146 with the lip 148 once again.

Upon insertion of the IUP catheter 10 into the uterus, fluid fills the space 32 between the outer hollow tube 16 and the inner tube 30, and the balloon 42 is in a substantially deflated state. With charging, the balloon 42 becomes at least partially filled with air. Thus, depending on how much air is in the balloon 42 prior to charging, the balloon 42 may be anywhere from 40% to 70% filled to capacity with air following charging. The volume of air which respectively fills the inner tube 30 and balloon 42 will vary, of course, with the size and length of the inner tube 30 and balloon 42. However, the volume of air in the air column is such that at least fifty percent of the air volume will remain in the balloon 42 with a 100 mm Hg increase in pressure. In prototype designs, for example, it was found that about a 200 microliter volume balloon, charged with about 100 microliters of air, provides satisfactory signals when an external pressure of 100 mm Hg is applied. It is desirable not to overfill balloon 42 and thereby introduce the structure of the balloon into the signal. In other words, the flaccidity of the partially-filled working volume of balloon 42 will prevent the occurrence of aberrant effects in pressure detection due to temperature changes as dictated by Charles's Law, or aberrant effects which might be introduced signal artifacts due to the balloon wall internal forces, or external balloon compression from debris.

The low durometer material of the balloon 42 allows the surface of the balloon 42 to deform with an increase in pressure. Therefore, an increase in intrauterine pressure generally greater than about 1 mm Hg will deform the balloon 42 and, in turn, modify the pressure in the air column within the balloon 42 and inner tube 30. The change is pressure is translated down the air column to the diaphragm 120 of the pressure sensor 102. Deflection of the diaphragm 120 resulting from an increase in pressure is converted to an electrical signal by the transducer and is relayed to the fetal monitor 86 through the cable 106. Similarly, a subsequent decrease in intrauterine pressure is also relayed by subsequent expansion of the balloon 42. Maximum uterine pressure win not fully collapse balloon 42 when the air column is charged.

It should be noted that "zeroing" is simplified with the present invention because atmospheric pressure exists on both sides of the diaphragm 120 prior to insertion of the male connector 72 into the female connector 98 because the internal bore 114 is exposed to atmosphere and the enclosure 100 behind diaphragm 120 is also exposed to atmosphere by virtue of an aperture 160 (FIG. 5) formed through the end cap 104 of the enclosure 100. Therefore, "true zero" exists prior to plugging the IUP catheter 10 into the reusable interface cable assembly 84, and "true zero," or zero differential across the membrane, can be attained at any time by simply disconnecting the catheter from the reusable connector, even when the catheter remains in the uterus. The simplicity of "zeroing" the device on an initial or continuing basis provides a significant advantage over prior art systems.

It may be noted that some suitable materials which may be used in manufacturing the balloon 42 may be permeable to air and water such that, over time, air may dissipate from the balloon 42. However, the materials from which the balloon may be made are of sufficiently low permeability that the balloon 42 will remain appropriately charged for satisfactory monitoring. Even if pressure within the air column should drop below the normative value during use, the IUP catheter 10 can be simply and quickly "re-charged" by disconnecting the male connector 72 from the female connector 98 and plugging it back in. The air column can thus be re-charged as often as necessary.

Catheter 10 is preferably packaged in a gamma-ray sterilized package, and is disposable after use. Interface cable assembly 84 is separately supplied, and may vary in electrical output characteristics, depending upon the fetal monitor with which it is to be associated. Stated another way, the electronics of assembly 84 may be varied as known in the art to provide an appropriate output signal from sensor 102 to monitor 86, which may comprise any commercially-available monitor, including by way of example only, the Hewlett-Packard Model 8040 and the Corometrics 115. The manufacturer and model number of the monitor is of no significance to the invention.

Figure 10:
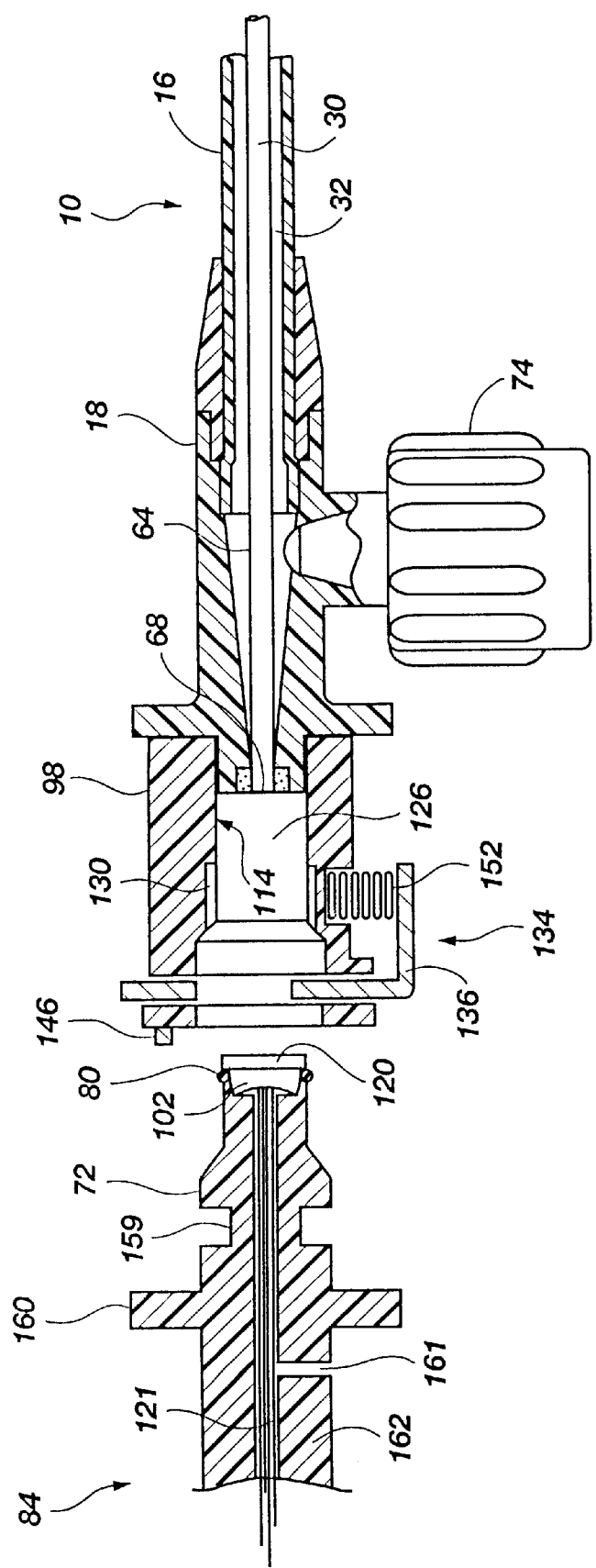
FIG. 10 is a view in cross section of an alternative embodiment of the invention where the connectors are differently structured.

In an alternative embodiment to that previously described, the housing 18 of the IUP catheter 10 may be formed as a female connector 98, as illustrated in FIG. 10 where like structures are shown in like reference numerals. Thus, the female connector 98 of the housing 18 may be formed with a bore 114 having an internal space 126 which is sized to receive the male connector 72 formed at the distal end of the reusable interface cable assembly 84. The pressure sensor 102 may be positioned at the distal extremity of the reusable interface cable 84, with the diaphragm 120 oriented toward the open proximal end 68 of the inner tube 30 upon insertion. Thus, as the male connector 72 of the reusable interface cable assembly 84 is inserted into the bore 114 of the female connector 98 of the housing 18 in the manner of a piston or plunger, the volume of air occupying the internal space 126 is displaced by the male connector 72. The displaced volume of air charges the air column, thereby partially inflating the balloon 42 with air, and excess air may be released from the internal space 126 as the O-ring associated with the male connector 72 contacts the wall of the bore 114 and forms an air-tight seal therewith. As previously described, the female connector 98 may be structured with locking device 134 comprising a slidable ring 136 which engages a groove 159 formed in the circumference of the male connector 72. A flange 160 formed about the circumference of the male connector 72 impacts against the detent 146 to engage the locking device 134, also as previously described. An aperture 161 is also formed through the wall 162 of the reusable interface cable assembly 84 to maintain ambient air pressure on the inner surface of the diaphragm 120.

FIG. 7 illustrates how the IUP catheter 10 of the present invention may be inserted into the intrauterine space 163 during labor to monitor changes in pressure. The IUP catheter 10 is inserted, using known techniques, by passing the tip 14 through the vagina and advancing the outer hollow tube 16 until the IUP catheter is inserted between thirty and forty-five centimeters, as measured from the tip 14. The removable sheath 20 is withdrawn from the distal end of the IUP catheter 10 and is removed from about the catheter 10. The male connector means 72 of the IUP catheter 10 is then inserted into the female connector means 98 of the reusable interface cable assembly 84 to charge the air column and the reusable interface cable assembly 84 is plugged into the fetal monitor 86 (FIG. 5). The IUP catheter 10 may then be secured to the leg 164 of the patient by appropriate means, such as a piece of tape 166.

The configuration illustrated in FIG. 7 allows the patient a certain amount of movement during the labor process, but essentially tethers the patient to the fetal monitor 86. Therefore, an alternative means of monitoring pressure data is illustrated in FIG. 8 where the male connector 72 of the IUP catheter 10 is attached to a female connector 98 as previously described (not shown in FIG. 8), the female connector means being mechanically attached to and electrically communicating with the transmitter 168, the transmitter 168 also housing the pressure sensor 102 (not shown in FIG. 8). Transmitter 168 transmits signal data corresponding to the detected changes in intrauterine pressure to a receiver 170 associated with a fetal monitor 86. The telemetry system as described preferably employs electromagnetic signals, and preferably low radio frequency signals, over a range of up to about forty feet. In this embodiment, the patient has greater mobility in moving around during labor.

Referencing FIGS. 11 and 12 of the drawings, extraovular and intra-amniotic placements of the tip or distal end of a pressure catheter are respectively illustrated for a better appreciation by the reader of the necessity for proper catheter tip placement in use of an intrauterine pressure catheter. FIG. 11 shows a catheter tip T, corresponding to tip 14 of the inventive catheter, disposed between the amniotic membranes M and the endometrial lining L of the uterus in an extraovular position and in isolation from the amniotic fluid space A. On the other hand, FIG. 12 shows proper, intra-amniotic placement of tip T within the amniotic fluid space A. Tip placement in accordance with FIG. 11 may produce a high baseline for the pressure signal, a damped waveform, and even negative pressure readings. Venting of a lumen through the catheter will not exhibit amniotic fluid. Tip placement in the amniotic fluid space in accordance with FIG. 12 will produce a good, low baseline and a crisp, easily readable waveform. Venting of a catheter lumen in this instance will exhibit amniotic fluid from the proximal end of the catheter.

FIG. 13 depicts an outer tube 216 in cross-section, the tube 216 including a light-transmissive window 220 extending about a 75 degree circumferential arc along the tube wall. The window 220 of the outer tube may be formed of clear PELLETHANE 2363 elastomer, while the remainder of the tube wall may be formed of HYTREL G6356 elastomer, by an extrusion process as known in the art. Alternatively, the entire tube 216 may be formed of a light-transmissive material 222 as shown in FIG. 13A. While it is preferred that the window 220 extend through substantially the entire length of the outer tube 216, it may extend along only a distal, proximal or medial portion thereof. Further, the window may comprise a series of discontinuous windows placed in longitudinally-spaced positions along the length of outer tube 216. FIG. 13B schematically depicts an outer tube 216 including discontinuous distal, medial and proximal windows 220a, 220b and 220c, respectively. Use of a window structure or other light-transmissive configuration for the outer catheter tube permits early viewing of amniotic fluid, prior to discharge thereof from the proximal end of the catheter, and thus facilitates safe confirmation of proper catheter placement. Such proper placement can prohibit dangerous clinical situations such as infusing into the extraovular space, causing abruptions, as well as inaccurate pressure readings.

Figure 14:
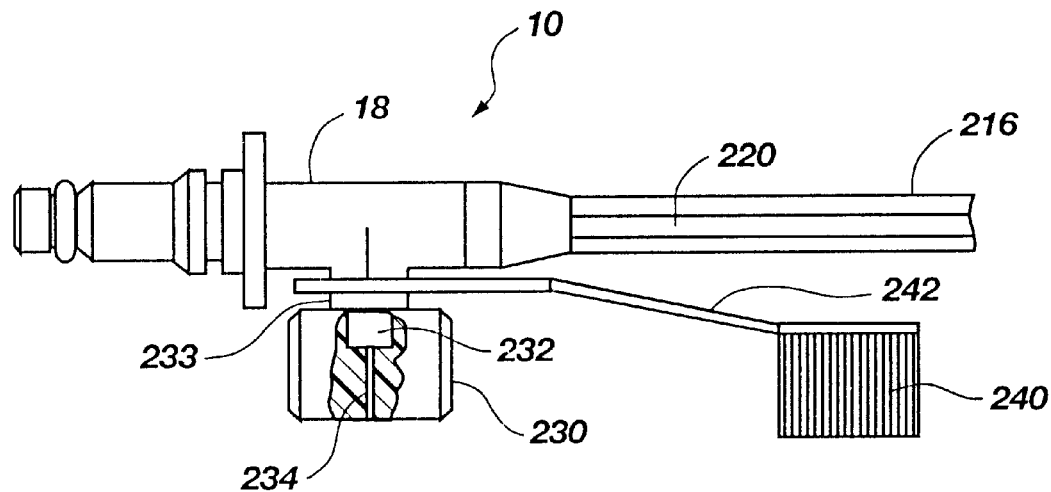
FIG. 14 is a side view of a proximal end of the catheter of the invention showing a venting closure in place and a tethered, unvented closure.

FIG. 14 illustrates a proximal end housing 18 for a catheter 10 preferably including an outer tube 216 having a window 220, although this is not a requirement. Venting cap 230 is shown in place over an amnio port 232 communicating with the interior of outer tube 216, the interior structure of housing 18 being as previously described. Venting cap 230 may be securable, for example, to the amnio port housing 233 through interior threads which may be made up with exterior threads on the amnio port housing 233. Alternatively, venting cap 230 may comprise a snap-on type closure. A small pin-hole 234 of, for example, 0.10 inch diameter, extends through cap 230 in communication with the interior of housing 18. Amniotic fluid will drip through pin-hole 234 under the differential pressure between the ambient atmosphere and intrauterine pressure when catheter tip 14 at distal end 12 of catheter 10 is properly placed. When proper catheter placement has been established, the vented cap 230 is replaced with a non-vented cap 240, preferably tethered at 242 to housing 18 as shown, after which the catheter 10 is attached, as previously described, to a reusable interface cable assembly 84 which has been properly zeroed according to the manufacturer's instructions.

Figure 15:
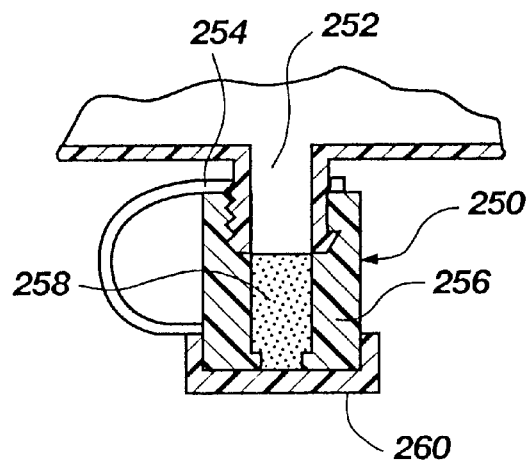
FIG. 15 is a side schematic cross-sectional view of a gas-permeable, liquid-impermeable, venting closure.

Referring now to FIG. 15, an alternative vented closure in the form of cap 250 is depicted in place over an amnio port 252 extending through port housing 254. As shown on the left-hand side of the figure, cap 250 may be secured by threads to port housing 254 or, as shown on the right-hand side of the figure, snapped over a lip on the exterior of housing 254. Cap 250 includes an outer sleeve 256 within which is disposed a porous element 258. As previously described, porous element 258 is preferably gas-permeable but liquid-impermeable (hydrophobic), so as to permit venting of air in the catheter to the atmosphere but prevent ejection of amniotic fluid, with attendant risk of pathogen exposure. One suitable material for porous element 258 is a high density polyethylene having a cellulose acetate coating (to render the polyethylene hydrophobic). Such a material is available from Porex Technologies Corp. of Fairburn, Ga., such material being designated as XM1374. One suitable porosity for providing passage for gas (air) present in space or channel 32 while precluding passage of pathogens resident in amniotic fluid passing to the proximal end of catheter 10 lies in about the 20 to 40 micron pore size range. If desired, cap 250 may be provided with a gas- and liquid-tight closure 260 which may be snapped thereover as shown prior to attachment of the catheter to a cable assembly rather than requiring removal of cap 250 and application of a separate closure to amnio port 252.

Using a venting closure as described above provides the additional advantage, as the space or lumen 32 is filled with amniotic fluid, of automatically providing a liquid coupling around balloon 42 to couple amniotic pressure external to catheter 10 to the exterior of balloon 42. The internal balloon design of catheter 10, with its protected balloon, is not sensitive to application of direct force (such as tissue pushing directly on a diaphragm), but only to amniotic pressure coupled through amniotic fluid providing the aforementioned liquid coupling. While all of the internal balloon embodiments of the invention as disclosed herein provide such an advantage, the use of a venting closure enhances this advantage.

The pressure catheter of the present invention provides significant improvements over prior intrauterine pressure catheter devices because it is simply constructed, is easy to use, is constructed for safe, comfortable and accurate insertion and simplifies zeroing, thereby avoiding constant recalibration. Moreover, the closed air column provides for isolation of the gas pressure-transfer medium from bodily fluids and fluids injected into the body of the patient. Thus, the pressure catheter of the present invention is suitable for detecting pressure changes in a number of medical procedures, including fetal monitoring during labor, intracranial pressure monitoring and arterial or venous pressure monitoring. Hence, reference herein to specific details of the illustrated embodiments is by way of example and not by way of limitation. It will be apparent to those skilled in the art that many additions, deletions and modifications to the illustrated embodiments of the invention may be made without departing from the spirit and scope of the invention as defined by the following claims. For example, the balloon may be widened and shortened to optimize volume and increase sensitivity, and disposed in an enlarged portion of the outer tube, or even within a molded "cage" between the distal end of the outer tube and the catheter tip.

Figure 16:
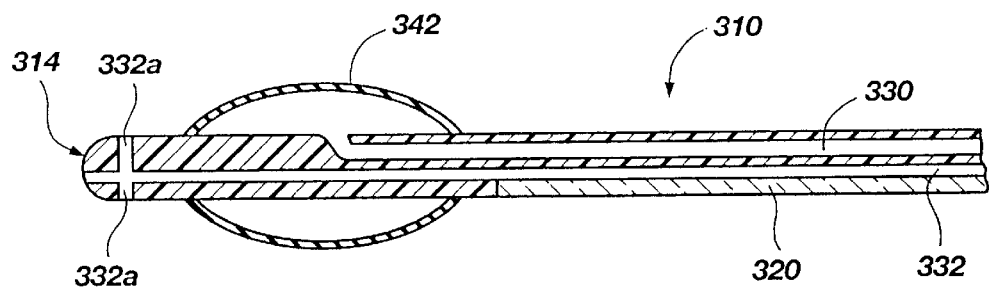
FIG. 16 is a side sectional view of an external balloon embodiment of the present invention.

For certain applications wherein contact with a vessel wall or other bodily element is unlikely to occur and thereby compromise accurate operation of the catheter, the balloon or other pressure-compliant member may be placed on the exterior of the catheter, as depicted in FIG. 16. FIG. 16 depicts a catheter 310 comprising an external balloon 342 and a single tube, dual-lumen design. Lumen 330 extends from the proximal end of catheter 310 to the interior of balloon 342 at the distal end thereof and communicates air thereto during charging of the closed air column defined by lumen 330 and balloon 342. Lumen 332 extends from the proximal end of catheter 310 to and through tip 314 and the distal end thereof, by way of example only. Additional side channels 332a also communicate with lumen 332 to provide multiple access thereto by amniotic fluid in the event of debris clogging one particular opening. Light-transmissive window 320 extends along at least a portion of catheter 310 between lumen 332 and the catheter exterior.

Figure 17:
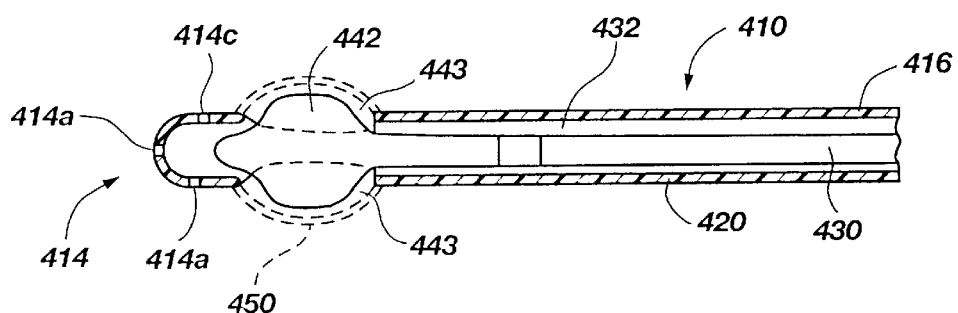
FIG. 17 is a side, partial sectional view of an exterior/interior balloon embodiment of the present invention.

Further, a portion of the balloon may be internal to the catheter, with the remainder external to the catheter, as depicted in FIG. 17. Catheter 410 includes an outer tube 416 surrounding an inner tube 430, to which is secured balloon 442 in a manner as previously described. Balloon 442 includes portions exterior to, as well as interior to, catheter 410. The exterior portions protrude through cut-outs 443 in the wall of outer tube 416. A lumen 432 is defined between outer tube 416 and inner tube 430, and view window 420 in the form of a light-transmissive outer housing material provides a view of fluid present in lumen 432. Tip 414 is provided with apertures 414a to promote fluid access to all exterior portions of balloon 442. Further, a "cage" 450 as depicted in broken lines may optionally be provided to protect balloon 442 from direct contact with tissue.

Simpler connectors may be used between the catheter and the cable assembly, and a plunger-type charging mechanism incorporated in the cable-end connector.

What is claimed is:

1. A pressure catheter for detecting changes in pressure within a body comprising:

an elongated outer tube defined by a circumferential wall, having a first end and a second end and encompassing a fluid channel extending longitudinally through an interior of said outer tube, apertures formed through said wall of said outer tube proximate said first end providing communication between an exterior of said elongated outer tube and said interior of said outer tube, at least a portion of said wall of said outer tube lying between said fluid channel and the exterior of said outer tube and located remote from said first end being formed of a light-transmissive material comprising at least one transmissive window along a length of said elongated tube structure;

a closed air column located at least partially within said outer tube, said air column extending longitudinally from proximate said first end of said outer tube to proximate said second end thereof;

a pressure-compliant member proximate said first end of said outer tube, said pressure-compliant member defining an interior chamber in communication with said closed air column, said pressure-compliant member being deformable with a change in fluid pressure external to said elongated outer tube relative to pressure of air within said closed air column; and said catheter including structure for substantially precluding direct contact of said pressure-compliant member with tissues of said body when inserted thereinto.

2. The pressure catheter of claim 1, further comprising structure for charging a selected volume of air into said closed air column and effecting closure thereof.

3. The pressure catheter of claim 2, wherein said closed air column is located within an elongated inner tube positioned within said elongated outer tube.

4. The pressure catheter of claim 3, wherein said pressure-compliant member comprises a thin-walled balloon formed of flexible material.

5. The pressure catheter of claim 3, wherein said structure for charging said air column includes a housing to which said inner tube is secured in sealing engagement therewith.

6. The pressure catheter of claim 5, wherein said housing includes a port therethrough in fluid communication with said fluid channel, said port having an exterior outlet.

7. The pressure catheter of claim 6, further including a venting closure configured for attachment to said housing over said exterior outlet.

8. The pressure catheter of claim 7, wherein said venting closure includes a pin-hole communicating between said port and an exterior of said venting closure.

9. The pressure catheter of claim 7, wherein said venting closure includes a porous element disposed between said port and an exterior of said venting closure, said porous element being permeable to gases and substantially impermeable to liquids.

10. The pressure catheter of claim 9, wherein said porous element is impermeable to pathogens.

11. The pressure catheter of claim 9, wherein said venting closure further includes a sealing member disposable over a surface of said porous element exposed on said exterior of said venting closure.

12. The pressure catheter of claim 1, further comprising a pressure detection sensor positioned in communication with said closed air column to detect a pressure change in said air column.

13. The pressure catheter of claim 1, further comprising structure disposed within said closed air column for collecting condensation therewithin.

14. The pressure catheter of claim 1, wherein said light-transmissive material of said at least one window is substantially transparent.

15. The pressure catheter of claim 1, wherein said at least one window comprises a plurality of longitudinally-spaced windows of light-transmissive material.

16. The pressure catheter of claim 1, wherein said at least one window of light-transmissive material extends through about a 75 degree arc circumferentially of said outer tube wall.

17. The pressure catheter of claim 1, wherein said at least a portion of said outer tube wall which is formed of light-transmissive material comprises substantially an entire wall of said outer tube.

18. The pressure catheter of claim 1, further comprising a soft, pliant tip formed on said first end of said elongated outer tube for insertion within a body.

19. The pressure catheter of claim 1, further including structure disposed within at least a portion of said closed air column for preventing total occlusion of said air column.

20. An intrauterine pressure catheter comprising:
an elongated outer tube having a plurality of holes formed at a distal end thereof, said outer tube having a fluid channel located therein, at least a portion of a wall of said outer tube lying between said fluid channel and an exterior surface of said elongated outer tube and remote from the distal end thereof comprising at least one window of light-transmissive material along a length of said outer tube;
a soft, pliant tip attached to said distal end of said outer tube;
an elongated inner tube positioned within said elongated outer tube;
a pressure-compliant member in communication with an interior of said inner tube;
an air column defined by the interior of said inner tube and said pressure-compliant member;
structure for charging a selected volume of air into said air column and closing said air column after said charging;
a pressure detection device positioned in communication with said air column after closure thereof for detecting pressure changes therein; and
structure for transmitting pressure detection signals generated by said pressure detection device to a fetal monitor.

21. The intrauterine pressure catheter of claim 20, wherein said pressure-compliant member is a thin-walled balloon of flexible material.

22. The intrauterine pressure catheter of claim 21, wherein said balloon is attached to said inner tube by a resilient structure.

23. The intrauterine pressure catheter of claim 21, further comprising a structure located within said air column for collecting moisture present therein.

24. The intrauterine pressure catheter of claim 23, wherein said moisture-collecting structure comprises an elongated line of hygroscopic material positioned within said inner tube.

25. The intrauterine pressure catheter of claim 24, wherein said hygroscopic material is nylon.

26. The intrauterine pressure catheter of claim 20, further comprising a housing secured to said inner tube and having a first connector element, and wherein said pressure detection device is associated with a second connector element sized to mate with said first connector element in air-tight registration therewith, said first and second connection elements comprising said charging structure.

27. The intrauterine pressure catheter of claim 26, wherein said pressure detection device includes a pressure transducer having a diaphragm exposed to said air column.

28. The intrauterine pressure catheter of claim 26, including locking structure for retaining said first connector element in air-tight registration with said second connector element.

29. The intrauterine pressure catheter of claim 26, wherein one of said first and second connector elements is structured with a male configuration and the other of said first and second connector elements is structured with a female configuration.

30. The intrauterine pressure catheter of claim 26, wherein said housing includes an amnio port opening onto an exterior thereof and in communication with said fluid channel.

31. The intrauterine pressure catheter of claim 30, further including a venting closure configured for attachment to said housing over said amnio port.

32. The intrauterine pressure catheter of claim 31, wherein said venting closure includes a pin-hole communicating between said amnio port and an exterior of said venting closure.

33. The intrauterine pressure catheter of claim 31, wherein said venting closure includes a porous element disposed between said amnio port and an exterior of said closure, said porous element being permeable to gases and substantially impermeable to liquids.

34. The intrauterine pressure catheter of claim 33, wherein said porous element is substantially impermeable to pathogens.

35. The intrauterine pressure catheter of claim 33, wherein the venting closure further includes a sealing member disposable over a surface of said porous element exposed on the exterior of said venting closure.

36. The intrauterine pressure catheter of claim 20, wherein said at least one window is substantially transparent.

37. The intrauterine pressure catheter of claim 20, wherein said at least one window comprises a plurality of longitudinally-spaced windows.

38. The intrauterine pressure catheter of claim 20, wherein said at least one window extends through about a 75 degree arc circumferentially of said outer tube wall.

39. The intrauterine pressure catheter of claim 20, wherein substantially the entire wall of said outer tube comprises a light-transmissive material.

40. The intrauterine pressure catheter of claim 20, further including structure disposed within at least a portion of said air column for preventing total occlusion thereof.

41. A pressure catheter for detecting changes in pressure within a body comprising:
an elongated tube structure defining first and second lumens extending longitudinally therethrough from proximate a first end of said elongated tube structure to proximate a second end thereof, said first lumen opening to an exterior of said catheter proximate said first end of said elongated tube structure, and said elongated tube structure including a wall disposed between said first lumen and an exterior surface of said elongated tube structure, at least a portion of said wall remote from said first end of said elongated tube structure comprising a light-transmissive material comprising at least one light-transmissive window along a length of said elongated tube structure; and
a pressure-compliant member associated with said second lumen proximate said first end, of said elongated tube structure, said pressure-compliant member being deformable with a change in fluid pressure external to said elongated tube structure relative to pressure of air within said second lumen.

42. The pressure catheter of claim 41, further comprising structure for charging a selected volume of air into said second lumen.

43. The pressure catheter of claim 42, wherein said structure for charging said second lumen includes a housing to which said second lumen is secured in sealing engagement therewith.

44. The pressure catheter of claim 43, wherein said housing includes a port therethrough in fluid communication with said first lumen, said port having an outlet on an exterior of said housing.

45. The pressure catheter of claim 44, further including a venting closure configured for attachment to said housing over said exterior outlet on said exterior of said housing.

46. The pressure catheter of claim 45, wherein said venting closure includes a pin-hole communicating between said port and an exterior of said venting closure.

47. The pressure catheter of claim 46, wherein said venting closure includes a porous element disposed between said port and the exterior of said venting closure, said porous element being permeable to gases and substantially impermeable to liquids.

48. The pressure catheter of claim 47, wherein said porous element comprises a hydrophobic material.

49. The pressure catheter of claim 47, wherein said porous element is substantially impermeable to pathogens.

50. The pressure catheter of claim 47, wherein the venting closure further includes a sealing member disposable over a surface of said porous element exposed on the exterior of said venting closure.

51. The pressure catheter of claim 41, wherein said second lumen lies substantially within an inner tube, and said first lumen lies substantially between an exterior of said inner tube and an interior of an outer tube within which said inner tube is at least partially disposed.

52. The pressure catheter of claim 41, wherein said first and second lumens are defined by mutually adjacent first and second tubes.

53. The pressure catheter of claim 41, wherein said pressure-compliant member comprises a thin-walled balloon formed of flexible material.

54. The pressure catheter of claim 41, further comprising a pressure detection sensor positioned in communication with said second lumen to detect a pressure change therein.

55. The pressure catheter of claim 41, further comprising structure disposed within said second lumen for collecting condensation therewithin.

56. The pressure catheter of claim 41, further comprising structure disposed within said second lumen for preventing total occlusion thereof.

57. The pressure catheter of claim 41, wherein said at least one window is substantially transparent.

58. The pressure catheter of claim 41, wherein said at least one window comprises a plurality of longitudinally-spaced windows.

59. The pressure catheter of claim 41, wherein said at least one window extends through about a 75 degree arc circumferentially of said wall.

60. The pressure catheter of claim 41, wherein the light-transmissive wall portion comprises substantially an entire exterior wall of said elongated tube structure.

61. The pressure catheter of claim 41, further comprising a soft, pliant tip formed on said first end of said elongated outer tube structure.

* * * * *